(12) United States Patent
Jiang

(10) Patent No.: US 12,274,890 B1
(45) Date of Patent: Apr. 15, 2025

(54) FACIAL BEAUTY MASK

(71) Applicant: Shenzhen Aixuli Technology Co., Ltd., Shenzhen (CN)

(72) Inventor: Ping Jiang, Hunan Province (CN)

(73) Assignee: Shenzhen Aixuli Technology Co., Ltd., Shenzhen (CN)

( * ) Notice: Subject to any disclaimer, the term of this patent is extended or adjusted under 35 U.S.C. 154(b) by 0 days.

(21) Appl. No.: 18/915,848

(22) Filed: Oct. 15, 2024

(30) Foreign Application Priority Data

Oct. 18, 2023 (CN) .......................... 202322793026.3
Sep. 25, 2024 (CN) .......................... 202422347289.6

(51) Int. Cl.
*A61N 5/06* (2006.01)

(52) U.S. Cl.
CPC .... *A61N 5/0616* (2013.01); *A61N 2005/0647* (2013.01); *A61N 2005/0652* (2013.01); *A61N 2005/0663* (2013.01)

(58) Field of Classification Search
CPC ...... A61B 18/20–18/28; A61N 5/06–2005/073
USPC .................................. 606/2–19; 607/88–94
See application file for complete search history.

(56) References Cited

U.S. PATENT DOCUMENTS

2005/0070977 A1\* 3/2005 Molina .................... A61N 2/02
607/88
2016/0310757 A1\* 10/2016 Pepitone .............. A61N 5/0617

FOREIGN PATENT DOCUMENTS

| CN | 117122825 | A | \* | 11/2023 |
| KR | 101597169 | B1 | \* | 2/2016 |
| KR | 101741067 | B1 | \* | 5/2017 |
| KR | 102097298 | B1 | \* | 4/2020 |

\* cited by examiner

*Primary Examiner* — Jonathan T Kuo
*Assistant Examiner* — Vynn V Huh

(57) ABSTRACT

A facial beauty mask includes a light source part and a mask main body. The mask main body is connected to the light source part. The mask main body is provided with a first hollow part and a second hollow part. The first hollow part is used for exposing eyes, and the second hollow part is used for exposing a nose and a mouth. The mask main body is also provided with a breathable hollow part. The breathable hollow part, the first hollow part and the second hollow part are spaced apart from each other. Therefore, when a user uses the light emitted by the light source part to shine on the face for facial beauty, the first hollow part can be used for exposing the eyes, so that the user's eyes can observe the outside. The second hollow part can be used for exposing the nose and the mouth.

16 Claims, 15 Drawing Sheets

FACIAL BEAUTY MASK

CROSS-REFERENCE TO RELATED APPLICATIONS

The application claims priority of Chinese patent application CN2023227930263, filed on Oct. 18, 2023, which is incorporated herein by reference in its entireties. The application also claims priority of Chinese patent application CN2024223472896, filed on Sep. 25, 2024, which is incorporated herein by reference in its entireties.

TECHNICAL FIELD

The present invention relates to the technical field of beauty equipment, particularly to a facial beauty mask.

BACKGROUND ART

Facial beauty aims to improve the aging, wrinkles, sagging and other skin problems of the face in various ways, which is generally achieved by using facial masks or facial beauty masks. With the development of technology, beauty projects such as photorejuvenation (i.e., skin rejuvenation with light) have emerged, which use the photodynamic principle to activate deep cells and make the facial skin better metabolized. After light is absorbed by the skin, enzymatic reactions are produced to promote cell metabolism, stimulate the proliferation of subcutaneous collagen, and achieve anti-aging effects on the face. However, the facial beauty masks currently available on the market cover the entire face of the user, with extremely poor breathability, making the entire face feel extremely hot and stuffy during the beauty process, and even making the entire face sweat, greatly affecting the user's experience. Therefore, there is an urgent need to provide a breathable and comfortable facial beauty mask on the market.

SUMMARY

In order to overcome the shortcomings of the prior art, a facial beauty mask is provided in the present invention, including a light source part and a mask main body. The mask main body is connected to the light source part. The mask main body is provided with a first hollow part and a second hollow part. The first hollow part is used for exposing eyes, and the second hollow part is used for exposing a nose and a mouth. The mask main body is also provided with a breathable hollow part. The breathable hollow part, the first hollow part and the second hollow part are spaced apart from each other.

As an improvement of the present invention, the mask main body is provided with a first top wall, a first bottom wall, and a first side wall connected to the first top wall and the first bottom wall. The breathable hollow part includes a first breathable part. The first breathable part is positioned between the first hollow part and the first top wall.

As an improvement of the present invention, the breathable hollow part also includes a second breathable part. The second breathable part is positioned between the first hollow part and the first side wall.

As an improvement of the present invention, the breathable hollow part also includes a third breathable part. The third breathable part is positioned between the first hollow part and the first bottom wall.

As an improvement of the present invention, the breathable hollow part includes a plurality of breathable hollow openings. The plurality of breathable hollow openings are spaced apart from each other.

As an improvement of the present invention, the breathable hollow openings are defined around the first hollow part and the second hollow part.

As an improvement of the present invention, the plurality of breathable hollow openings at least include a first breathable opening unit and a second breathable opening unit. The first breathable opening unit and the second breathable opening unit are different in shape.

As an improvement of the present invention, the plurality of breathable hollow openings also include a third breathable opening unit. The first breathable opening unit, the second breathable opening unit, and the third breathable opening unit are different from each other in shape. The plurality of breathable hollow openings also include a fourth breathable opening unit. The first breathable opening unit, the second breathable opening unit, the third breathable opening unit, and the fourth breathable opening unit are different from each other in shape.

As an improvement of the present invention, the breathable hollow part, the first hollow part, and the second hollow part are different from each other in shape.

As an improvement of the present invention, the facial beauty mask further includes an eye rest bracket. The eye rest bracket is equipped with an eye rest main body part, a left eye rest part, and a right eye rest part. The left eye rest part and the right eye rest part are both connected to the eye rest main body part. The eye rest main body part is connected to the mask main body.

As an improvement of the present invention, the eye rest main body part, the left eye rest part, and the right eye rest part are integrally formed.

As an improvement of the present invention, the first hollow part includes a first left eye hollow opening and a first right eye hollow opening. The left eye rest part is provided with a second left eye hollow opening, and the right eye rest part is provided with a second right eye hollow opening. The second left eye hollow opening is aligned with the first left eye hollow opening, and the second right eye hollow opening is aligned with the first right eye hollow opening.

As an improvement of the present invention, the facial beauty mask further includes an eye rest bracket. The eye rest bracket is provided with a first front surface and a first rear surface. The first front surface is connected to the mask main body, and a spacing is defined between the first rear surface and the mask main body.

As an improvement of the present invention, the eye rest bracket is a flexible eye rest bracket. The eye rest bracket is an opaque eye rest bracket.

As an improvement of the present invention, the second hollow part includes a relatively narrow upper portion and a relatively wide lower portion, so that a relatively narrow nose hollow opening is formed at an upper end of the second hollow part, and a relatively wide mouth hollow opening is formed at a lower end of the second hollow part. The nose hollow opening and the mouth hollow opening are in communication with each other.

As an improvement of the present invention, the facial beauty mask further includes a light-transmissible cover layer. The cover layer is connected to the mask main body, and the cover layer covers the light source part. The mask main body is provided with a power port and a power input terminal. The power input terminal is positioned at the power port. The power input terminal is electrically connected to the light source part, and the power input terminal is positioned between the cover layer and the mask main body. The mask main body is integrally formed, and the cover layer is integrally formed. When the cover layer is integrally formed, at least one part of the cover layer is attached to a surface of the mask main body and connected to the mask main body, and a position limiting cavity is formed between the cover layer and the mask main body. The power input terminal is positioned inside the position limiting cavity. As an improvement of the present invention, a plurality of protruding parts extend from the surface of the mask main body. The plurality of protruding parts are spaced apart from each other, and a light source installation groove is formed between the plurality of protruding parts. The light source part is positioned inside the light source installation groove, and the light source part is connected to the mask main body. The cover layer is positioned inside the light source installation groove, and the light source part is positioned between the cover layer and the mask main body. The cover layer seals and covers the light source part inside the light source installation groove. The protruding parts include a plurality of first protruding units, a plurality of second protruding units, a plurality of third protruding units, and a plurality of fourth protruding units. The first protruding unit extends from an edge of the first breathable opening unit, the second protruding unit extends from an edge of the second breathable opening unit, the third protruding unit extends from an edge of the third breathable opening unit, and the fourth protruding unit extends from an edge of the fourth breathable opening unit. The light source part includes a plurality of LED light-emitting beads. The first protruding unit, the second protruding unit, the third protruding unit, and the fourth protruding unit are arranged at intervals around the LED light-emitting bead.

As an improvement of the present invention, the facial beauty mask further includes a tightening band. The tightening band is provided with a first end and a second end. The first end is connected to one side of the mask main body, and the second end is connected to an opposite side of the mask main body. A tightening space for wearing is surrounded and formed between the tightening band and the mask main body. One side of the mask main body is provided with a first hanging opening, and an opposite side of the mask main body is provided with a second hanging opening. The first end passes through the first hanging opening and is detachably connected to the tightening band, and the second end passes through the second hanging opening and is detachably connected to the tightening band, so that the mask main body and the tightening band are combined into a whole.

As an improvement of the present invention, the tightening band is equipped with a plurality of adjustment connection parts. The plurality of adjustment connection parts are arranged in sequence from the first end to the second end. The first end passes through the first hanging opening and is connected to one of the plurality of adjustment connection parts. The second end passes through the second hanging opening and is connected to one of the plurality of adjustment connection parts, so that a size of the tightening space is adjusted. An inner surface of the tightening band is provided with a hook and loop fastener, and the plurality of adjustment connection parts are a plurality of hook bands of the hook and loop fastener. The first end is equipped with a first hook engaging band, and the second end is equipped with a second hook engaging band. The first hook engaging band passes through the first hanging opening and is connected to one of the plurality of hook bands. The second hook engaging band passes through the second hanging opening and is connected to one of the plurality of hook bands.

As an improvement of the present invention, the tightening band is provided with a middle part, a left part, and a right part. The left part is connected to one side of the middle part, and the right part is connected to an opposite side of the middle part. The first end is provided on the left part, and the second end is provided on the right part. The middle part, the left part, and the right part are integrally formed.

As an improvement of the present invention, the tightening band is provided with the middle part, the left part, and the right part. The left part is connected to one side of the middle part, and the right part is connected to the opposite side of the middle part. The first end is positioned on the left part, and the second end is positioned on the right part. A width of the middle part is greater than a width of the left part and a width of the right part.

As an improvement of the present invention, the middle part is provided with a long strip-shaped fifth breathable opening unit.

As an improvement of the present invention, the cover layer is a light-transmissible silicone cover layer.

As an improvement of the present invention, the mask main body is an opaque silicone mask main body, and the eye rest bracket is an opaque silicone eye rest bracket.

Beneficial effects of the present invention are as follows. The facial beauty mask is provided in the present invention, including the light source part and the mask main body. The mask main body is connected to the light source part. The mask main body is provided with the first hollow part and the second hollow part. The first hollow part is used for exposing the eyes, and the second hollow part is used for exposing the nose and the mouth. The mask main body is also provided with the breathable hollow part. The breathable hollow part, the first hollow part and the second hollow part are spaced apart from each other. Therefore, when a user uses the light emitted by the light source part to shine on the face for facial beauty, the first hollow part can be used for exposing the eyes, so that the user's eyes can observe the outside. The second hollow part can be used for exposing the nose and mouth, so that the user's nose and mouth can breathe normally. Moreover, due to the arrangement of the breathable hollow part, the breathability of the entire mask main body is stronger, allowing the user's face to breathe and dissipate heat not only in the eyes, mouth, and nose, but also in other parts of the face other than the eyes, mouth and nose. Compared with a regular mask that covers the entire face, the wearing comfort of the facial beauty mask is greatly improved. Furthermore, the breathable hollow part can also play a role in weight reduction, making a weight of the facial beauty mask only about one-third of other masks on the market, so that the user will not feel a sense of falling or pressure when wearing the facial beauty mask, making it more comfortable to use and also saving materials for producing the beauty mask, making it more environmentally friendly.

BRIEF DESCRIPTION OF THE DRAWINGS

Implementations of the present disclosure will now be described, by way of embodiment, with reference to the attached figures. It should be understood, the drawings are shown for illustrative purpose only, for ordinary person skilled in the art, other drawings obtained from these draw

DETAILED DESCRIPTION OF THE EMBODIMENTS

Figure 1:
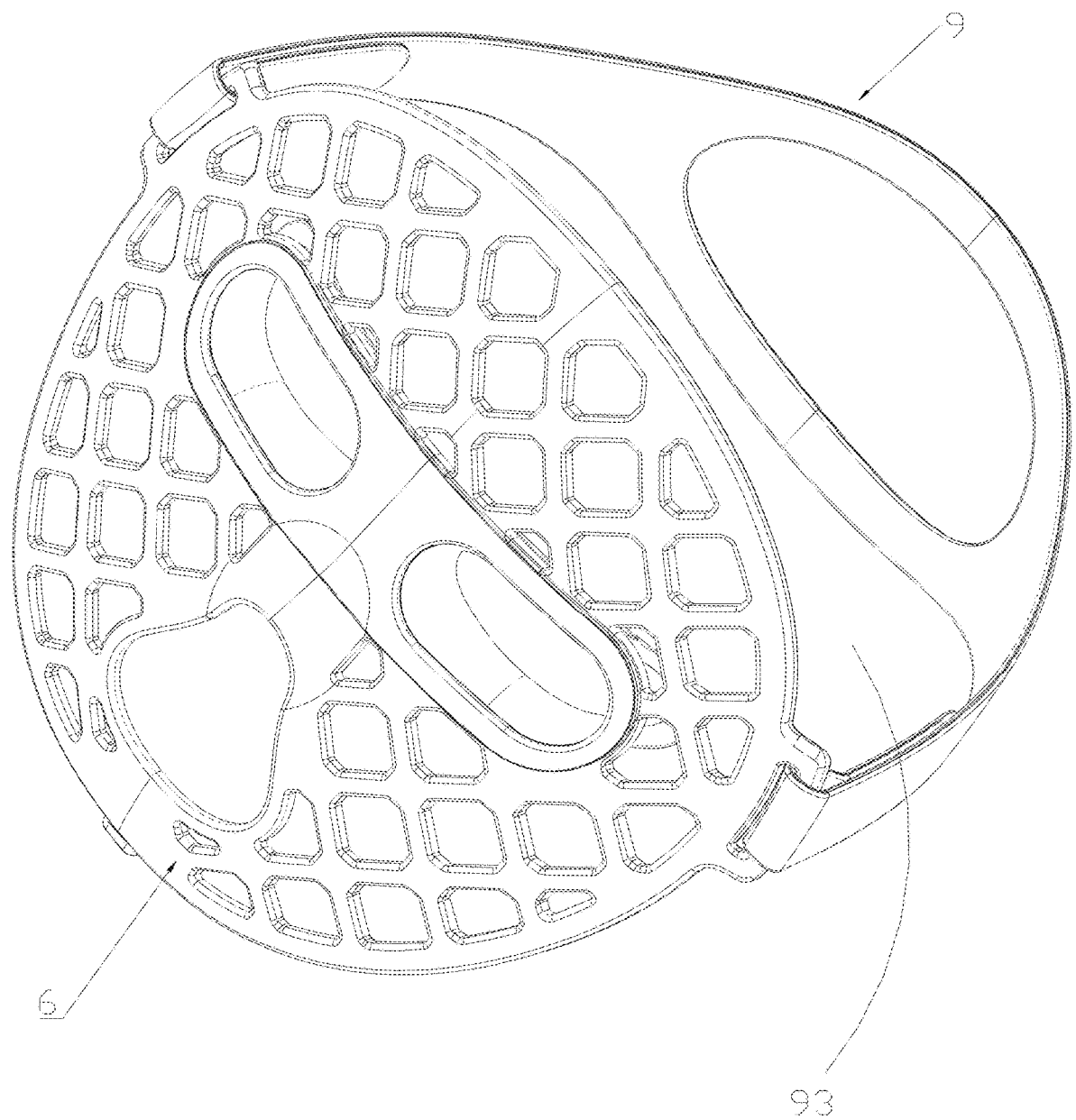
- FIG. 1 is a schematic diagram of an overall structure of the present invention.

It will be appreciated that for simplicity and clarity of illustration, where appropriate, reference numerals have been repeated among the different figures to indicate corresponding or analogous elements. In addition, numerous specific details are set forth in order to provide a thorough understanding of the exemplary embodiments described herein. However, it will be understood by those of ordinary skill in the art that the exemplary embodiments described herein may be practiced without these specific details. In other instances, methods, procedures, and components have not been described in detail so as not to obscure the related relevant feature being described. Also, the description is not to be considered as limiting the scope of the exemplary embodiments described herein. The drawings are not necessarily to scale and the proportions of certain parts may be exaggerated to better illustrate details and features of the present disclosure.

The term "comprising" when utilized, means "including, but not necessarily limited to"; it specifically indicates open-ended inclusion or membership in the so-described combination, group, series, and the like. The disclosure is illustrated by way of example and not by way of limitation in the figures of the accompanying drawings in which like references indicate similar elements. It should be noted that references to "an" or "one" embodiment in this disclosure are not necessarily to the same embodiment, and such references can mean "at least one". In addition, the terms "first" and "second" are used for descriptive purposes only and cannot be understood as indicating or implying relative importance or implying the number of indicated technical features. Thus, the features defined as "first" and "second" may explicitly or implicitly include one or more of the features. In the description of embodiments of the application, "a plurality of" means two or more, unless otherwise specifically defined.

Embodiment One

Figure 2:
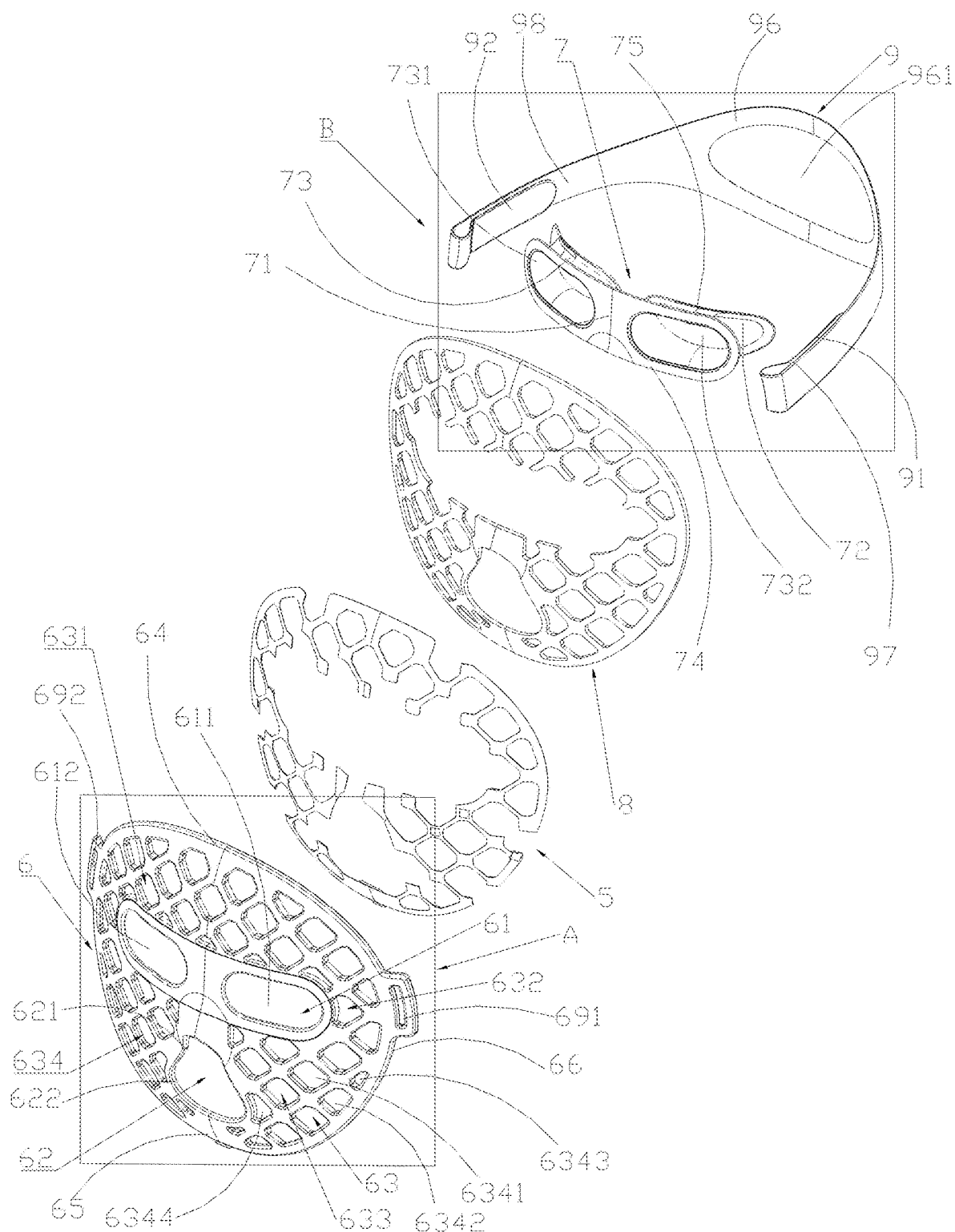
FIG. 2 is an exploded view of the present invention.
Figure 3:
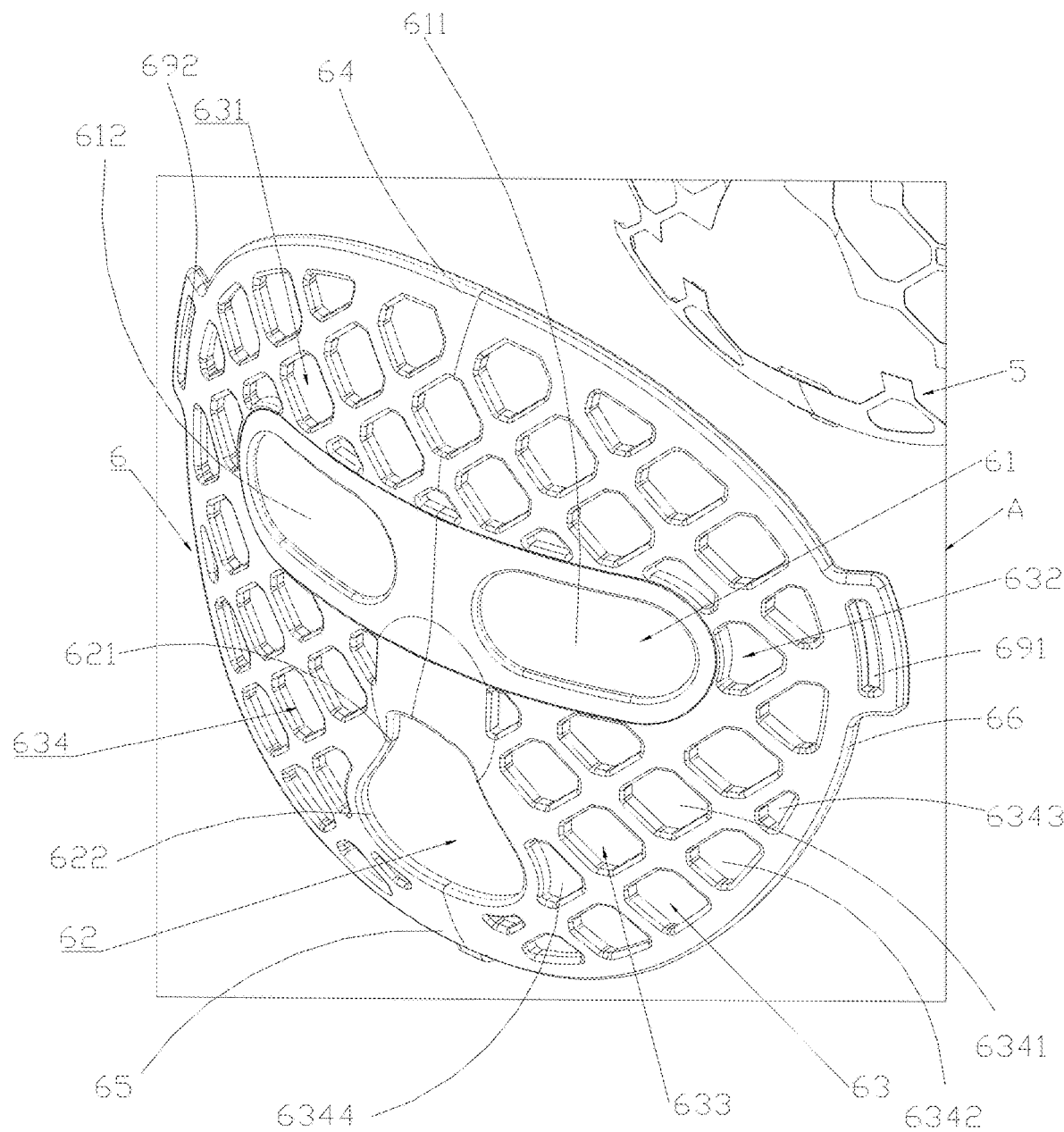
FIG. 3 is an enlarged view of area A in FIG. 2.
Figure 4:
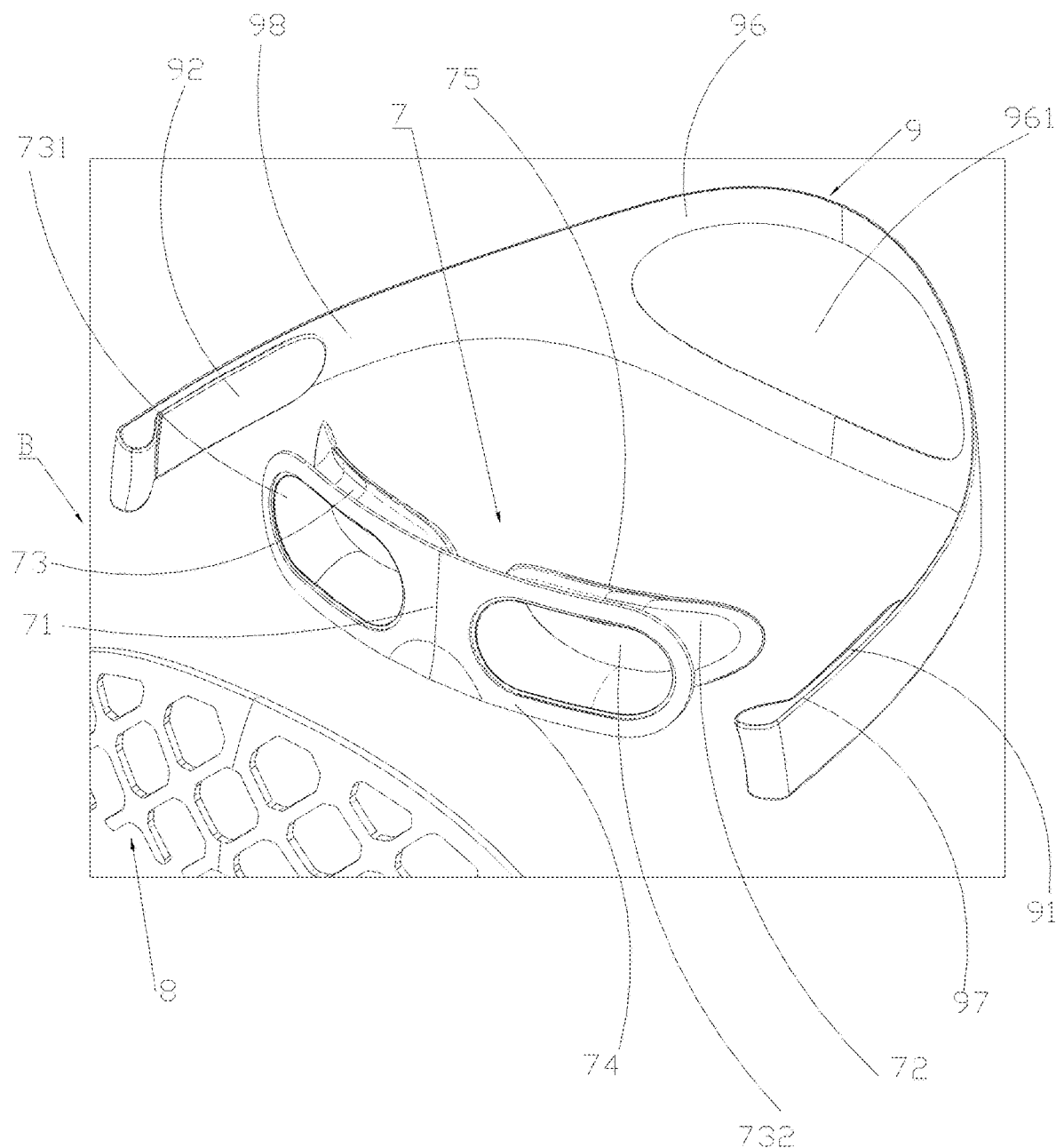
FIG. 4 is an enlarged view of area B in FIG. 2.
Figure 5:
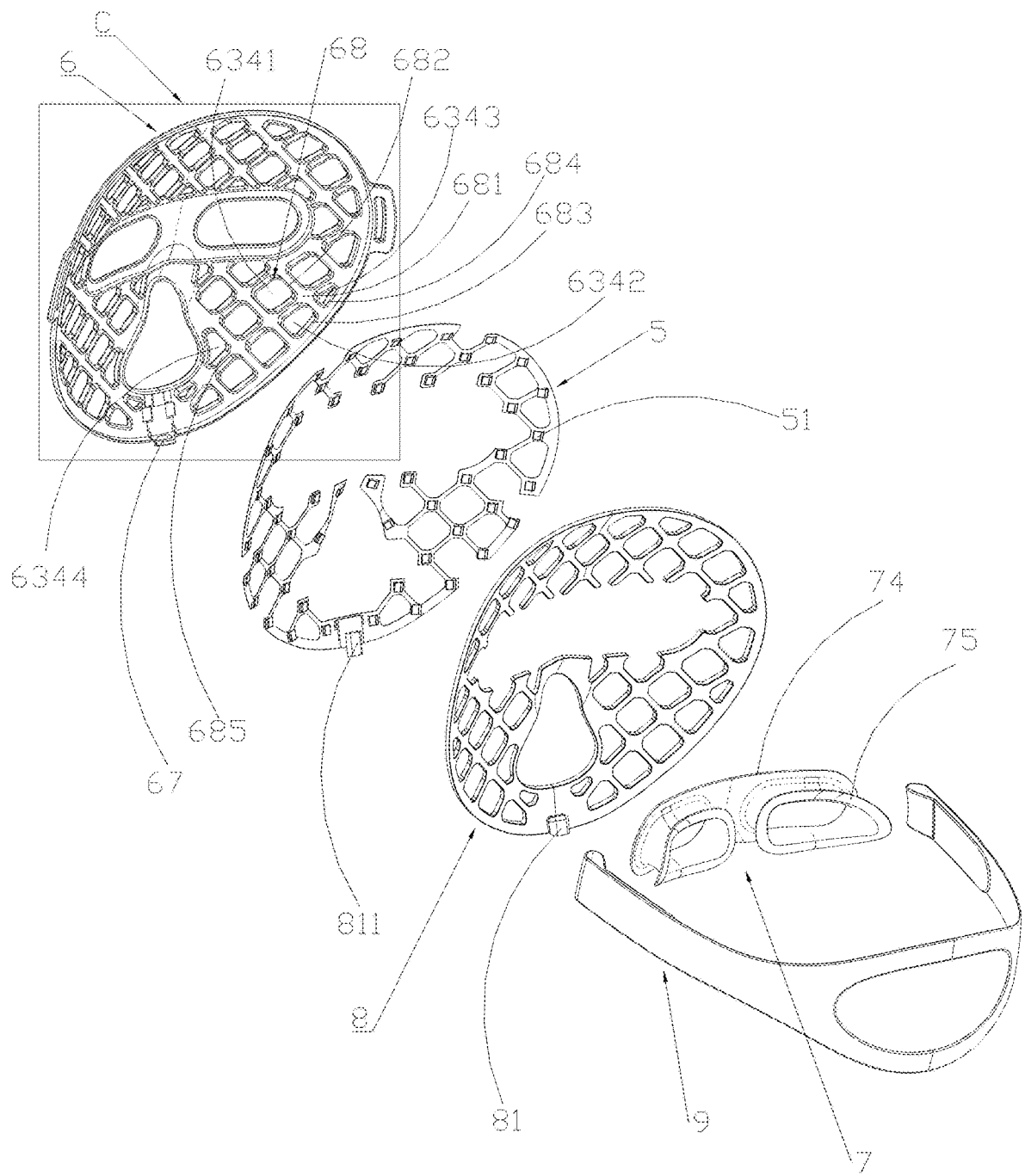
FIG. 5 is another exploded view of the present invention.
Figure 6:
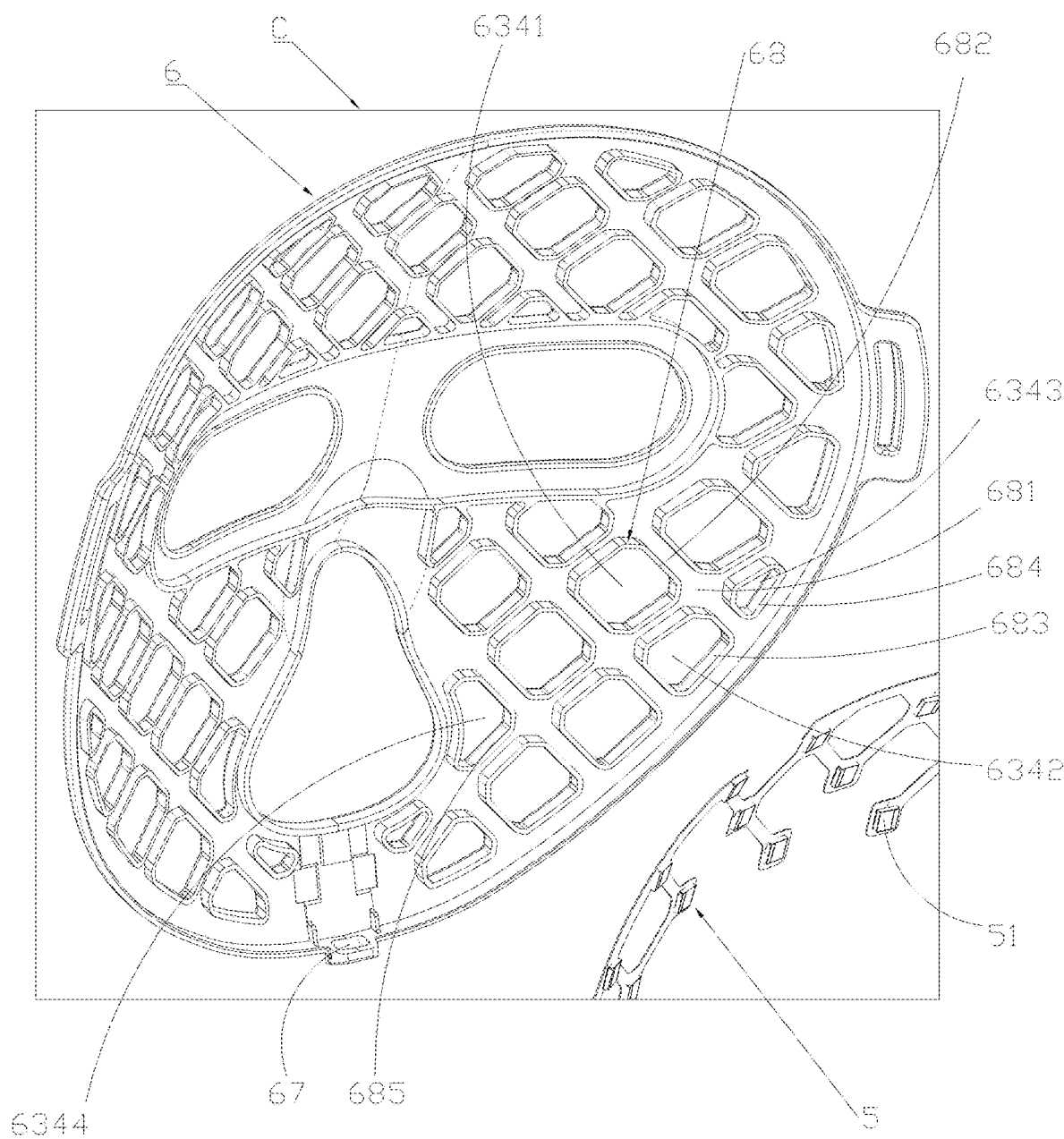
FIG. 6 is an enlarged view of area C in FIG. 5.
Figure 7:
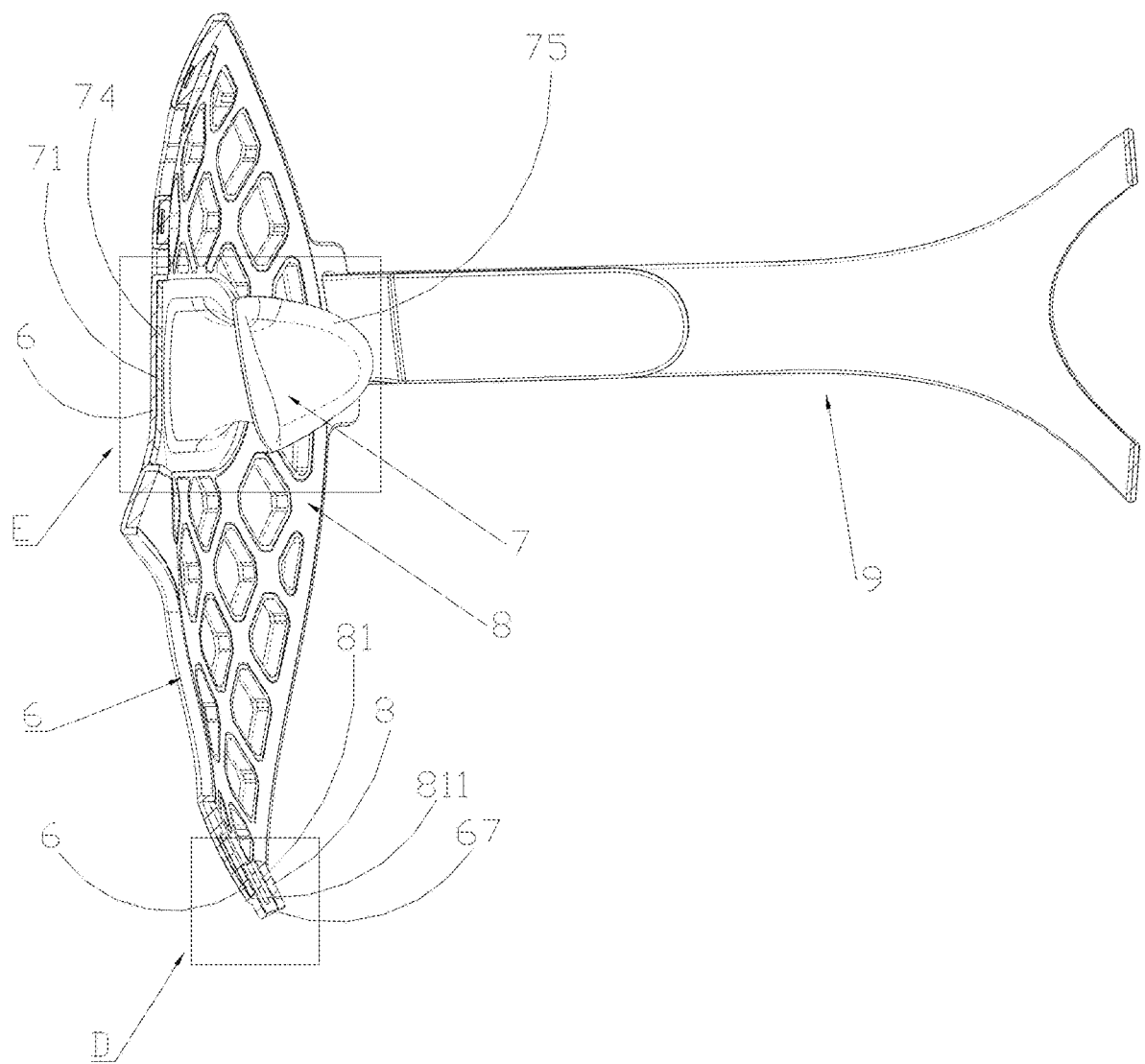
FIG. 7 is a sectional view cut along a mask main body and a power input terminal.
Figure 8:
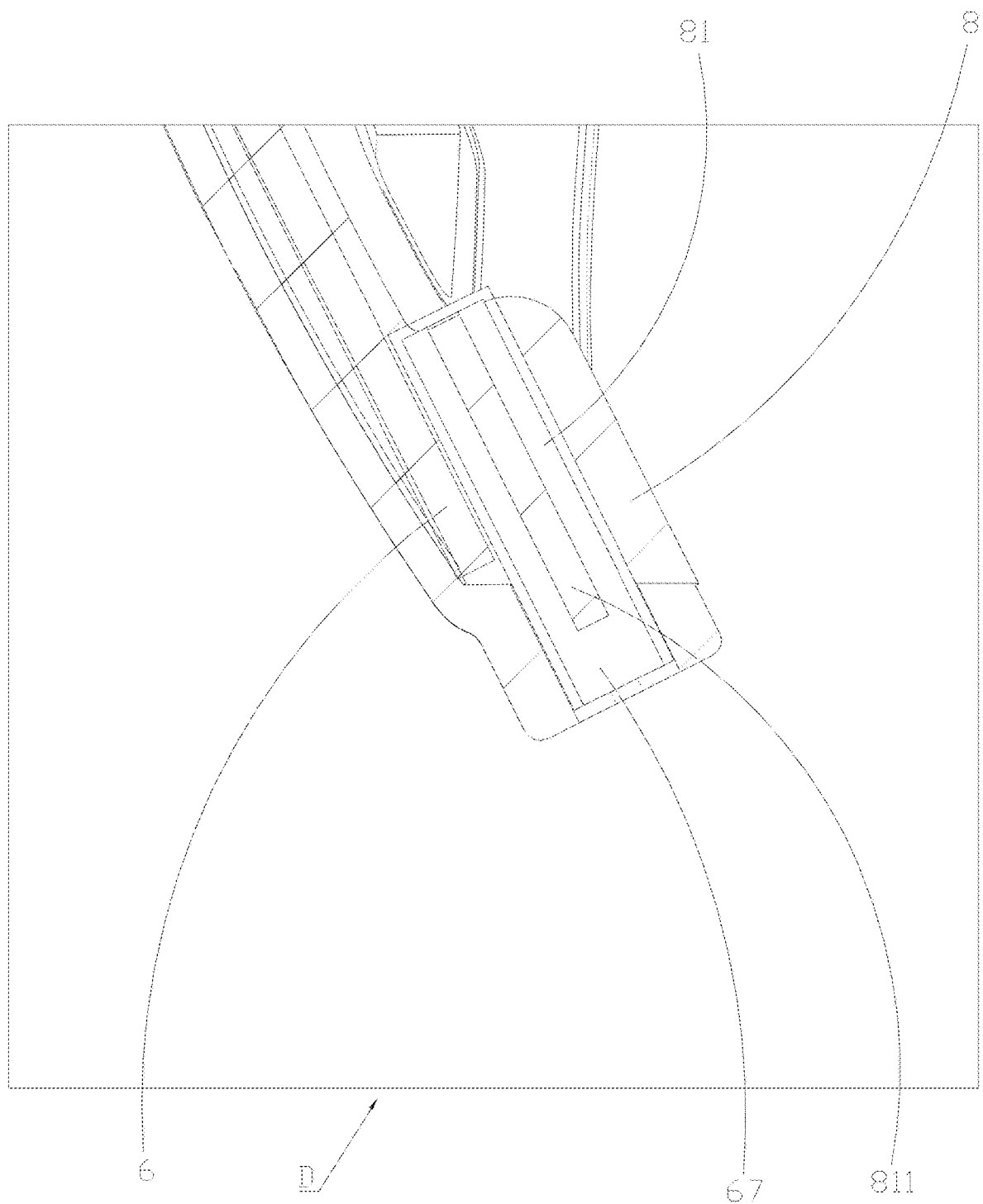
FIG. 8 is an enlarged view of area D in FIG. 7.
Figure 9:
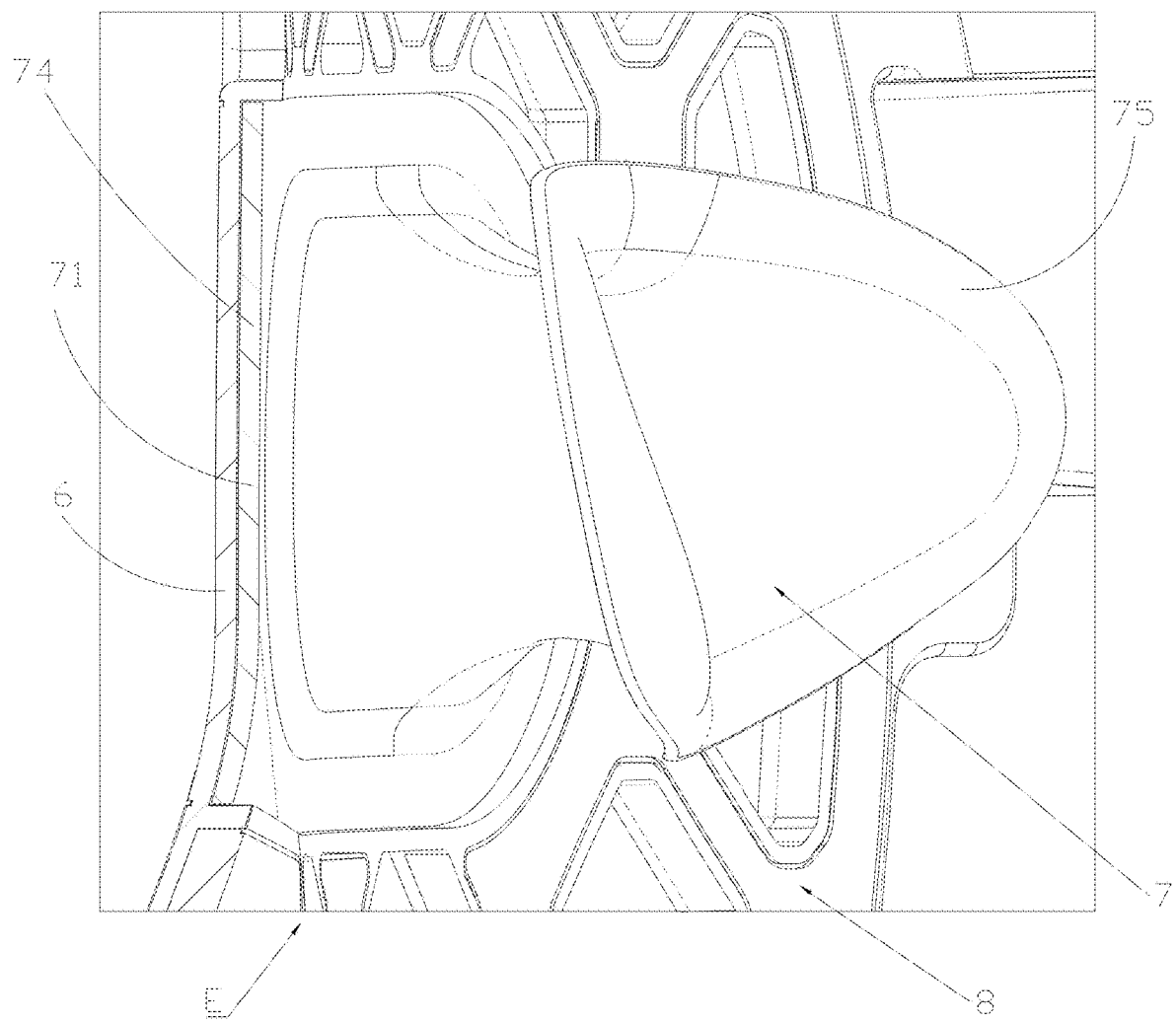
FIG. 9 is an enlarged view of area E in FIG. 7.
Figure 10:
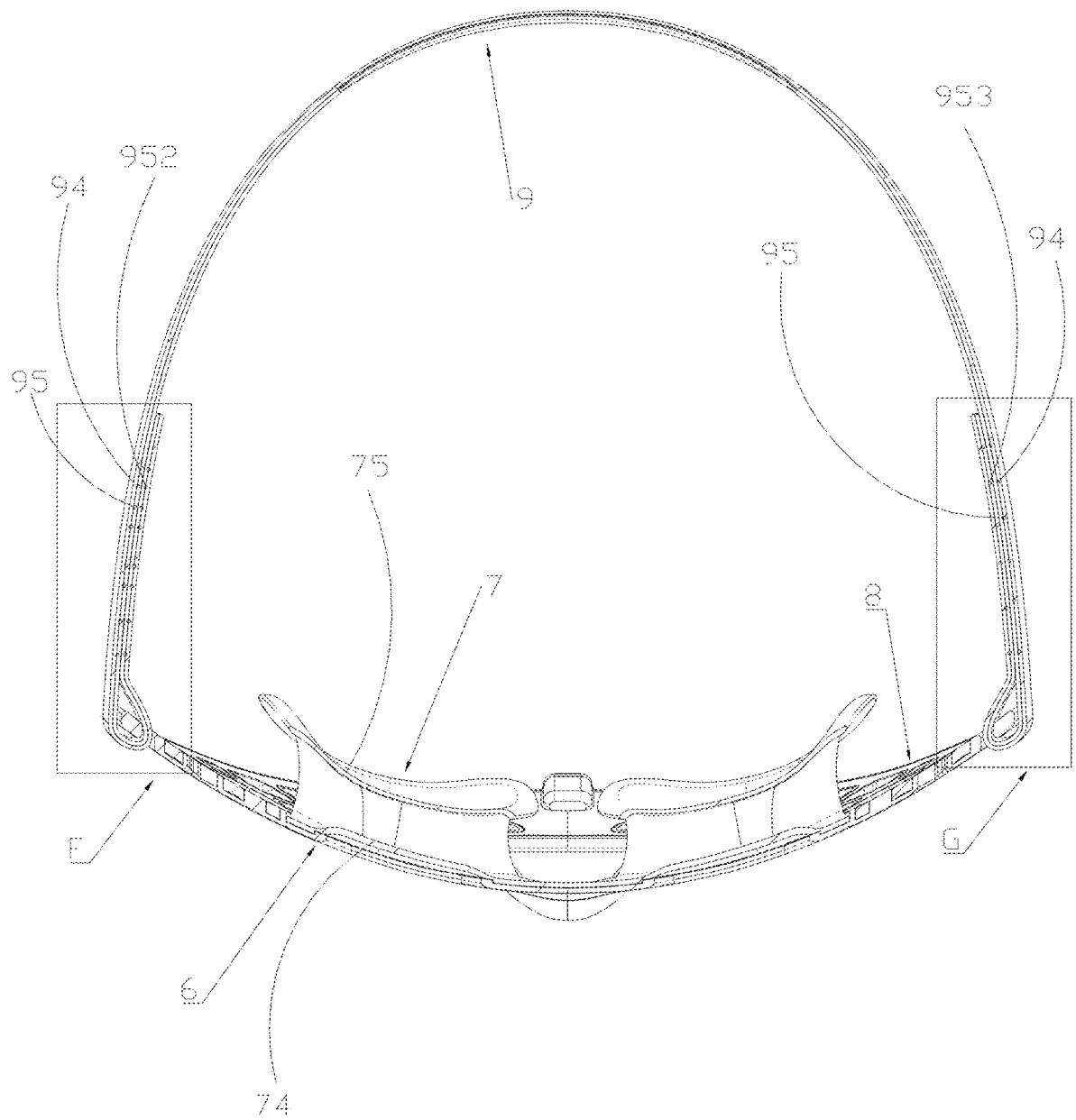
FIG. 10 is a sectional view cut along a mask main body and a tightening band.
Figure 11:
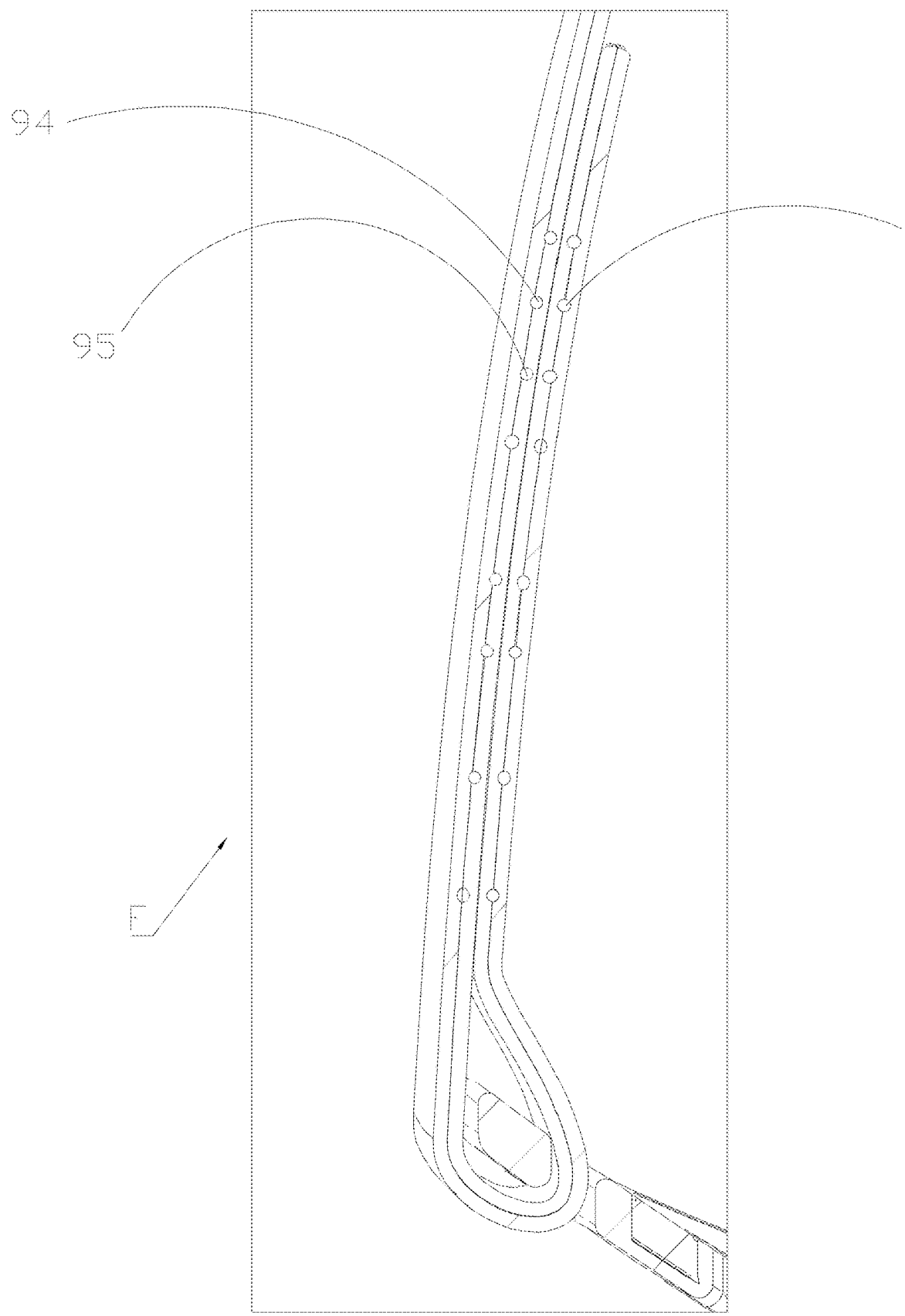
FIG. 11 is an enlarged view of area F in FIG. 10.
Figure 12:
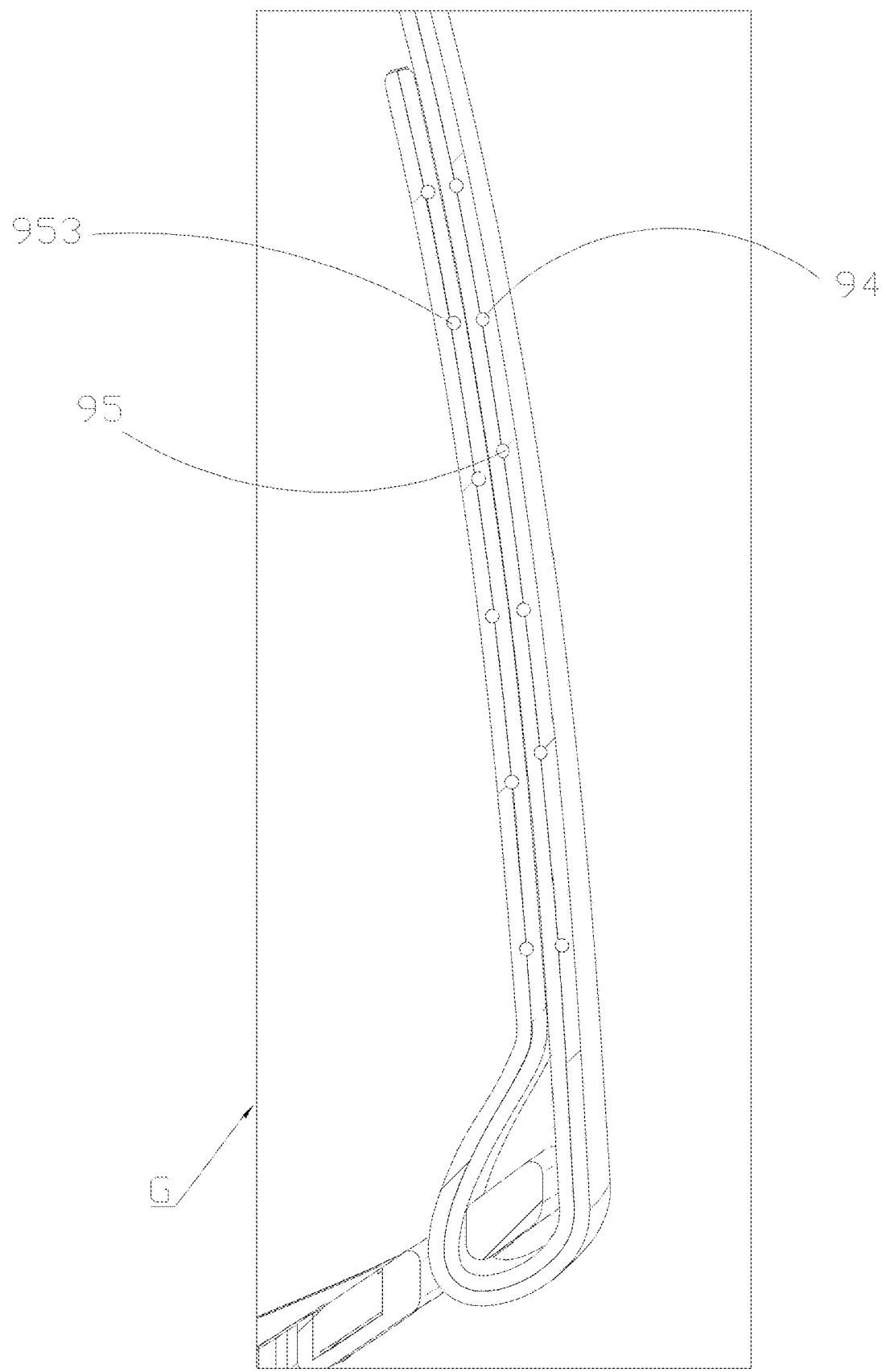
FIG. 12 is an enlarged view of area G in FIG. 10.

Referring to FIGS. 1-12, a facial beauty mask includes a light source part 5 and a mask main body 6. The mask main body 6 is connected to the light source part 5. The mask main body 6 is provided with a first hollow part 61 and a second hollow part 62. The first hollow part 61 is used for exposing eyes, and the second hollow part 62 is used for exposing a nose and a mouth. The mask main body 6 is also provided with a breathable hollow part 63. The breathable hollow part 63, the first hollow part 61 and the second hollow part 62 are spaced apart from each other.

Through the above structure, the facial beauty mask includes the light source part 5 and the mask main body 6. The mask main body 6 is connected to the light source part 5. The mask main body 6 is provided with the first hollow part 61 and the second hollow part 62. The first hollow part 61 is used for exposing the eyes, and the second hollow part 62 is used for exposing the nose and the mouth. The mask main body 6 is also provided with the breathable hollow part 63. The breathable hollow part 63, the first hollow part 61 and the second hollow part 62 are spaced apart from each other. Therefore, when a user uses the light emitted by the light source part 5 to shine on the face for facial beauty, the first hollow part 61 can be used for exposing the eyes, so that the user's eyes can observe the outside. For example, the user can watch videos through the first hollow part 61 during the beauty process. The second hollow part 62 can be used for exposing the nose and mouth, so that the user's nose and mouth can breathe normally. Moreover, due to the arrangement of the breathable hollow part 63, the breathability of the entire mask main body 6 is stronger, allowing the user's face to breathe and dissipate heat not only in the eyes, mouth, and nose, but also in other parts of the face other than the eyes, mouth and nose. Compared with a regular mask that covers the entire face, the wearing comfort of the facial beauty mask is greatly improved. Furthermore, the breathable hollow part can also play a role in weight reduction, making a weight of the facial beauty mask only about one-third of other masks on the market, so that the user will not feel a sense of falling or pressure when wearing the facial beauty mask, making it more comfortable to use and also saving materials for producing the beauty mask, making it more environmentally friendly.

In this embodiment, the mask main body 6 is provided with a first top wall 64, a first bottom wall 65, and a first side wall 66 connected to the first top wall 64 and the first bottom wall 65. The breathable hollow part 63 includes a first breathable part 631. The first breathable part 631 is positioned between the first hollow part 61 and the first top wall 64. The breathable hollow part 63 also includes a second breathable part 632. The second breathable part 632 is positioned between the first hollow part 61 and the first side wall 66. Specifically, the breathable hollow part 63 also includes a third breathable part 633. The third breathable part 633 is positioned between the first hollow part 61 and the first bottom wall 65. Through the above structure, the first breathable part 631 positioned between the first hollow part 61 and the first top wall 64 can facilitate the heat dissipation of the user's forehead, the second breathable part 632 positioned between the first hollow part 61 and the first side wall 66 can facilitate the heat dissipation around the user's eyes, and the third breathable part 633 positioned between the first hollow part 61 and the first bottom wall 65 can facilitate the heat dissipation of the cheek area, the area around the nose and the area around the mouth, so that the user's entire face can breathe and dissipate heat when using the beauty mask for beauty, keeping the entire face dry and comfortable.

In this embodiment, the breathable hollow part 63 includes a plurality of breathable hollow openings 634. The plurality of breathable hollow openings 634 are spaced apart from each other. The breathable hollow openings 634 are defined around the first hollow part 61 and the second hollow part 62. Specifically, the plurality of breathable hollow openings 634 at least include a first breathable opening unit 6341 and a second breathable opening unit 6342. The first breathable opening unit 6341 and the second breathable opening unit 6342 are different in shape. Furthermore, the plurality of breathable hollow openings 634 also include a third breathable opening unit 6343. The first breathable opening unit 6341, the second breathable opening unit 6342, and the third breathable opening unit 6343 are different from each other in shape. The plurality of breathable hollow openings 634 also include a fourth breathable opening unit 6344. The first breathable opening unit 6341, the second breathable opening unit 6342, the third breathable opening unit 6343, and the fourth breathable opening unit 6344 are different from each other in shape. Furthermore, the breathable hollow part 63, the first hollow part 61, and the second hollow part 62 are different from each other in shape. Through the above structure, due to the different shapes of the first breathable opening unit 6341, the second breathable opening unit 6342, the third breathable opening unit 6343, and the fourth breathable opening unit 6344, the entire mask main body 6 can be filled with breathable openings as much as possible, further improving the breathability of the mask main body 6.

In this embodiment, the facial beauty mask further includes an eye rest bracket 7. The eye rest bracket 7 is equipped with an eye rest main body part 71, a left eye rest part 72, and a right eye rest part 73. The left eye rest part 72 and the right eye rest part 73 are both connected to the eye rest main body part 71. The eye rest main body part 71 is connected to the mask main body 6. The eye rest main body part 71, the left eye rest part 72, and the right eye rest part 73 are integrally formed. Specifically, the first hollow part 61 includes a first left eye hollow opening 611 and a first right eye hollow opening 612. The left eye rest part 72 is provided with a second left eye hollow opening 732, and the right eye rest part 73 is provided with a second right eye hollow opening 731. The second left eye hollow opening 732 is aligned with the first left eye hollow opening 611, and the second right eye hollow opening 731 is aligned with the first right eye hollow opening 612. Furthermore, the facial beauty mask further includes an eye rest bracket 7. The eye rest bracket 7 is provided with a first front surface 74 and a first rear surface 75. The first front surface 74 is connected to the mask main body 6, and a spacing is defined between the first rear surface 75 and the mask main body 6. Furthermore, the eye rest bracket 7 is a flexible eye rest bracket 7. The eye rest bracket 7 is an opaque eye rest bracket 7. Through the above structure, the opaque eye rest bracket 7 can prevent the light emitted by the light source part 5 from shining on the human eye, protecting the user's eyes and improving the comfort of wearing the beauty mask. Moreover, the eye rest main body part 71, the left eye rest part 72, and the right eye rest part 73 that are integrally formed can be easily produced and have higher strength, and can better support the user's eyes.

Furthermore, a spacing is defined between the first rear surface 75 of the eye rest bracket 7 and the mask main body 6, so that when the first rear surface 75 of the eye rest bracket 7 is fitted with the user's eyes, the user's eyes and the entire face are spaced apart from the first front surface 74 and the mask main body 6, which further improves the breathability of the mask main body 6 and facilitates the divergence of the light for beauty emitted by the light source part 5, providing more sufficient irradiation to the face and effectively enhancing the beauty effect of the mask main body 6.

In this embodiment, the second hollow part 62 includes a relatively narrow upper portion and a relatively wide lower portion, so that a relatively narrow nose hollow opening 621 is formed at an upper end of the second hollow part 62, and a relatively wide mouth hollow opening 622 is formed at a lower end of the second hollow part 62. The nose hollow opening 621 and the mouth hollow opening 622 are in communication with each other. Through the above structure, since the nose hollow opening 621 and the mouth hollow opening 622 are in communication with each other, compared with a nose hollow opening 621 and a mouth hollow opening 622 which are separated from each other, the nose hollow opening 621 and the mouth hollow opening 622 which are in communication with each other not only have good breathability effect, but can also better adapt to the shape of the user's nose and mouth, further improving the comfort of wearing the beauty mask.

In this embodiment, the facial beauty mask further includes a light-transmissible cover layer 8. The cover layer 8 is connected to the mask main body 6, and the cover layer 8 covers the light source part 5. The mask main body 6 is provided with a power port 67 and a power input terminal 811. The power input terminal 811 is positioned at the power port 67. The power input terminal 811 is electrically connected to the light source part 5, and the power input terminal 811 is positioned between the cover layer 8 and the mask main body 6. The mask main body 6 is integrally formed, and the cover layer 8 is integrally formed. When the cover layer 8 is integrally formed, at least one part of the cover layer 8 is attached to a surface of the mask main body 6 and connected to the mask main body 6, and a position limiting cavity 81 is formed between the cover layer 8 and the mask main body 6. The power input terminal 811 is positioned inside the position limiting cavity 81. Through the above structure, the arrangement of the power input terminal 811 is effectively achieved, so that the user can supply power to the light source part 5 through the power input terminal 811. Moreover, since the power input terminal 811 is positioned within the position limiting cavity 81, a position of the power input terminal 811 can be effectively prevented from shifting. Furthermore, the mask main body 6 is integrally formed, the cover layer 8 is integrally formed, when the cover layer 8 is integrally formed, at least one part of the cover layer 8 is attached to the surface of the mask main body 6 and connected to the mask main body 6, the position limiting cavity 81 is formed between the cover layer 8 and the mask main body 6, and the power input terminal 811 is positioned within the position limiting cavity 81, so that the connection between the mask main body 6, the light source part 5 and the cover layer 8 is effectively achieved, and electronic components such as the light source part 5 and the power input terminal 811 can be sealed, thereby effectively improving the waterproof effect of the beauty mask. The power input terminal 811 is a TYPE-C or USB power input terminal 811.

In this embodiment, a plurality of protruding parts 68 extend from the surface of the mask main body 6. The plurality of protruding parts 68 are spaced apart from each other, and a light source installation groove 681 is formed between the plurality of protruding parts 68. The light source part 5 is positioned inside the light source installation groove 681, and the light source part 5 is connected to the mask main body 6. The cover layer 8 is positioned inside the light source installation groove 681, and the light source part 5 is positioned between the cover layer 8 and the mask main body 6. The cover layer 8 seals and covers the light source part 5 inside the light source installation groove 681. The protruding parts 68 include a plurality of first protruding units 682, a plurality of second protruding units 683, a plurality of third protruding units 684, and a plurality of fourth protruding units 685. The first protruding unit 682 extends from an edge of the first breathable opening unit 6341, the second protruding unit 683 extends from an edge of the second breathable opening unit 6342, the third protruding unit 684 extends from an edge of the third breathable opening unit 6343, and the fourth protruding unit 685 extends from an edge of the fourth breathable opening unit 6344. The light source part 5 includes a plurality of LED light-emitting beads 51. The first protruding unit 682, the second protruding unit 683, the third protruding unit 684, and the fourth protruding unit 685 are arranged at intervals around the LED light-emitting bead 51. The LED light-emitting beads 51 can be red LED light-emitting beads 51 or blue LED light-emitting beads 51, etc., which are used for providing irradiation of beauty light to the skin. Through the above structure, since the light source part 5 is positioned between the cover layer 8 and the mask main body 6, the cover layer 8 seals and covers the light source part 5 in the light source installation groove 681, which not only effectively completes the arrangement of the LED light-emitting beads 51, but also makes the overall beauty mask more flat and beautiful.

In this embodiment, the facial beauty mask further includes a tightening band 9. The tightening band 9 is provided with a first end 91 and a second end 92. The first end 91 is connected to one side of the mask main body, and the second end 92 is connected to an opposite side of the mask main body. A tightening space 93 for wearing is surrounded and formed between the tightening band 9 and the mask main body 6. One side of the mask main body 6 is provided with a first hanging opening 691, and an opposite side of the mask main body 6 is provided with a second hanging opening 692. The first end 91 passes through the first hanging opening 691 and is detachably connected to the tightening band 9, and the second end 92 passes through the second hanging opening 692 and is detachably connected to the tightening band 9, so that the mask main body 6 and the tightening band 9 are combined into a whole. The tightening band 9 is equipped with a plurality of adjustment connection parts 94. The plurality of adjustment connection parts 94 are arranged in sequence from the first end 91 to the second end 92. The first end 91 passes through the first hanging opening 691 and is connected to one of the plurality of adjustment connection parts 94. The second end 92 passes through the second hanging opening 692 and is connected to one of the plurality of adjustment connection parts 94, so that a size of the tightening space 93 is adjusted. An inner surface of the tightening band 9 is provided with a hook and loop fastener 95, and the plurality of adjustment connection parts 94 are a plurality of hook bands of the hook and loop fastener 95. The first end 91 is equipped with a first hook engaging band 952, and the second end 92 is equipped with a second hook engaging band 953. The first hook engaging band 952 passes through the first hanging opening 691 and is connected to one of the plurality of hook bands. The second hook engaging band 953 passes through the second hanging opening 692 and is connected to one of the plurality of hook bands. Through the above structure, the first hook engaging band 952 passes through the first hanging opening 691 and is connected to one of the plurality of hook bands, and the second hook engaging band 953 passes through the second hanging opening 692 and is connected to one of the plurality of hook bands, so that the size of the tightening space 93 can be adjusted, making the beauty mask more versatile, facilitating the wearing of the beauty mask on different sizes of heads, and making it convenient for the user to adjust the tightness of the wearing.

In this embodiment, the tightening band 9 is provided with a middle part 96, a left part 97, and a right part 98. The left part 97 is connected to one side of the middle part 96, and the right part 98 is connected to an opposite side of the middle part 96. The first end 91 is provided on the left part 97, and the second end 92 is provided on the right part 98. The middle part 96, the left part 97, and the right part 98 are integrally formed. The tightening band 9 is provided with the middle part 96, the left part 97, and the right part 98. The left part 97 is connected to one side of the middle part 96, and the right part 98 is connected to the opposite side of the middle part 96. The first end 91 is positioned on the left part 97, and the second end 92 is positioned on the right part 98. A width of the middle part 96 is greater than a width of the left part 97 and a width of the right part 98. Through the above structure, since the middle part 96, the left part 97, and the right part 98 are integrally formed, the strength of the tightening band 9 is improved, allowing the user to wear the beauty mask more stably on the head. Moreover, since the width of the middle part 96 is greater than the width of the left part 97 and the width of the right part 98, a contact area between the tightening band 9 and the head can be increased to improve the comfort of wearing.

In this embodiment, the middle part 96 is provided with a long strip-shaped fifth breathable opening unit 961. Through the above structure, the tightening band 9 can be made more breathable and heat dissipating, improving the comfort of wearing.

In this embodiment, the cover layer 8 is a light-transmissible silicone cover layer 8. The mask main body 6 is an opaque silicone mask main body 6, and the eye rest bracket 7 is an opaque silicone eye rest bracket 7. Through the above structure, the cover layer 8 is the light-transmissible silicone cover layer 8, the mask main body 6 is the opaque silicone mask main body 6, and the eye rest bracket 7 is the opaque silicone eye rest bracket 7, so that the mask main body 6, the cover layer 8 and the eye rest bracket 7 which are made of silicone are safe and environmentally friendly, can be washed repeatedly, and are not easy to age or breed bacteria.

Embodiment Two

Figure 13:
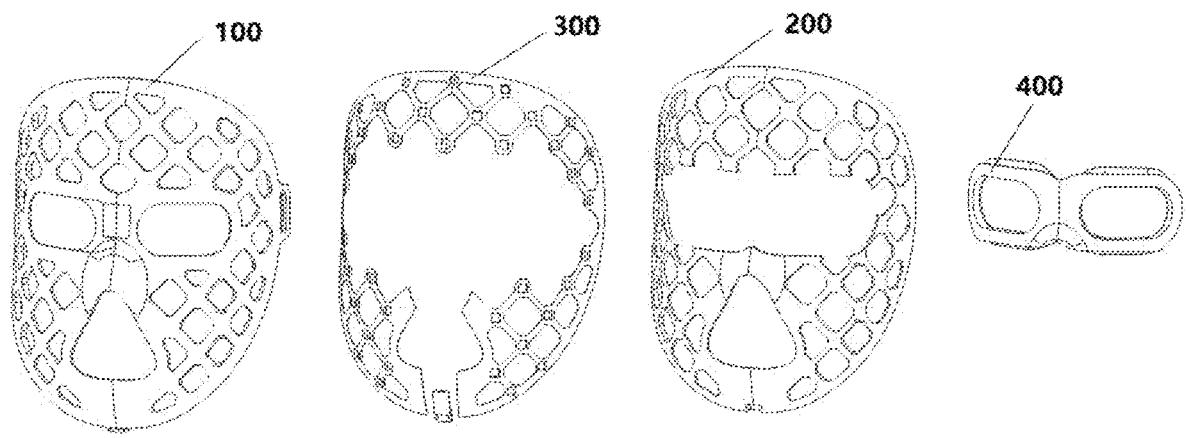
FIG. 13 is an exploded view of a structure of an ultra light liquid silicone beauty mask according to an embodiment of the present invention.
Figure 14:
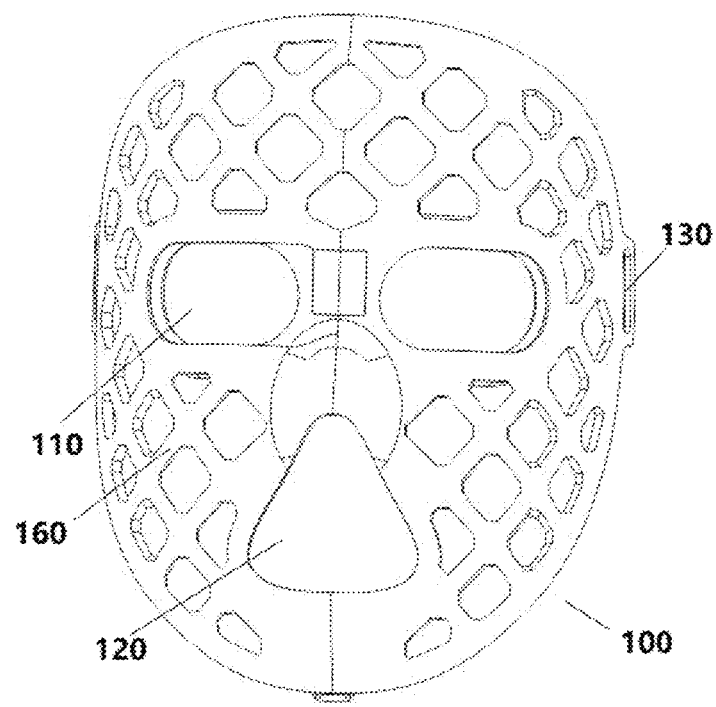
FIG. 14 is a schematic diagram of a structure of a non-facial contact surface of a first mask according to an embodiment of the present invention.
Figure 15:
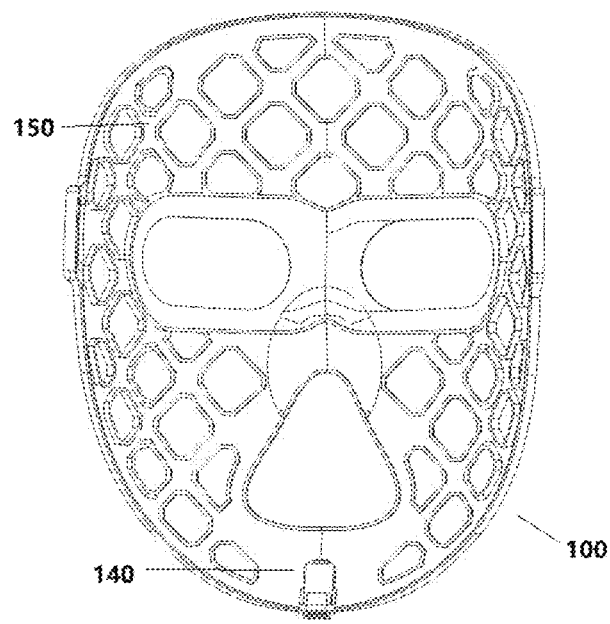
FIG. 15 is a schematic diagram of a structure of a facial contact surface of a first mask according to an embodiment of the present invention.
Figure 16:
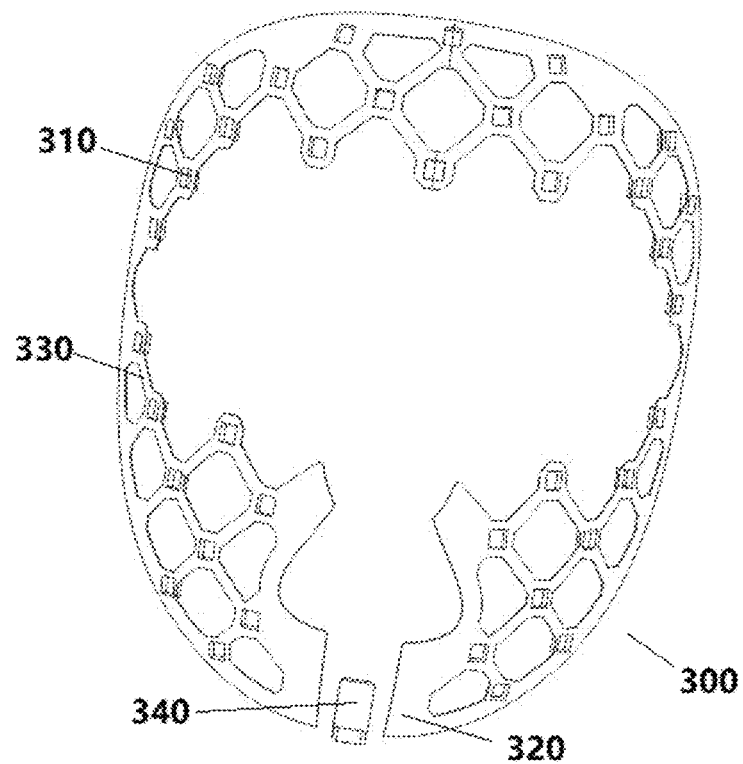
FIG. 16 is a schematic diagram of a structure of a circuit layer according to an embodiment of the present invention.
Figure 17:
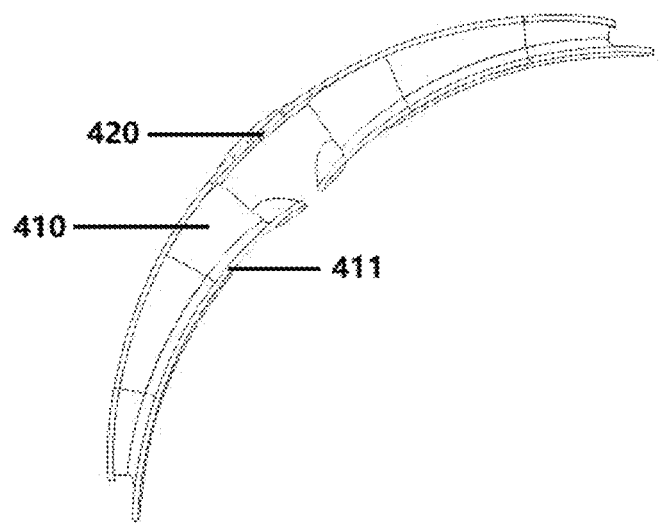
FIG. 17 is a schematic diagram of a structure of an eye protection cover according to an embodiment of the present invention.

Referring to FIGS. 13-17, an ultra light liquid silicone beauty mask is further provided in the present invention, including a first mask 100 in an outer layer not in contact with a face, a middle circuit layer 300, and a second mask 200 in an inner layer in contact with the face. The ultra light liquid silicone beauty mask further includes an eye protection mask 400 that is detachably connected to eye hollow openings 110. The first mask 100 is equipped with two left-right symmetrical eye hollow openings 110 and one nose and mouth hollow opening 120. The eye hollow opening 110 is used for installing the eye protection cover 400, and is used in conjunction with the eye protection cover 400 to protect the eyes and facilitate observation during actual use. The nose and mouth hollow opening 120 is used for breathing, ensuring normal communication and breathing for the user during use.

The first mask 100 and the circuit layer 300 are respectively connected by a peripheral silicone strip 160 and a wire 330 to form an outer ring. Two sets of obliquely parallel silicone strips 160 and wires 330 are vertically cross-connected to each other inside the ring, respectively. The silicone strip 160 forms a grid-like frame of the mask main body 6 between the outer ring, the eye hollow opening 110, and the nose and mouth hollow opening 120, making the whole lighter in weight, more easily deformed under the action of force, and easier to fit with the face. An installation groove 150 with nodes cross-communicated is formed on a facial contact surface for installing the circuit layer 300 and the second mask 200. The wire 330 forms a grid-like communicated circuit in the outer ring and areas avoiding the eye hollow opening 110 and the nose and mouth hollow opening 120. Lamp beads 310 are arranged at cross nodes. When powered on, the lamp beads 310 can emit light to activate deep cells, promote better metabolism of facial skin, and stimulate the proliferation of subcutaneous collagen, to achieve anti-aging and beauty effects on the face. Moreover, arranging light beads 310 at the cross nodes can ensure that a total number of the light beads 310 is sufficient to cover and fit the face within a light emitting range. The circuit layer 300 and the second mask 200 are both arranged in the installation groove 150.

This technical solution adopts a grid format design with the silicone strips 160 vertically cross-connected to each other, making the overall weight of the beauty mask lighter. At the same time, the detachable eye protection cover 400 is used in conjunction to provide comprehensive protection for the human eye.

As shown in FIGS. 14-17, the eye protection cover 400 is equipped with two left-right symmetrical sealing frames 410. An eye sealing ring 411 is arranged on the sealing frame 410. The sealing frames 410 are integrally connected through a connection part 420. The sealing frames 410 can allow the user to maintain normal visual senses while using the mask, and avoid personal injury caused by the light generated by the lamp beads 310. The eye sealing ring 411 in contact with an eye periphery is closely attached to the eye periphery, avoiding light leakage of the eye protection cover 400, and further protecting the eyes while improving wearing comfort. A material of the first mask 100 and a material of the eye protection mask 400 are flexible and opaque liquid silicone. A material of the second mask 200 is liquid silicone that is flexible and has good light transmittance. Liquid silicone not only has excellent properties such as high temperature resistance, cold resistance, and electrical insulation of solid silicone, but also has fluidity. Liquid silicone used in the beauty mask can enhance the flexibility of the mask, making the mask easier to bend and deform under external forces, and easy to restore to its previous state without external forces. The first mask 100 and the eye protection mask 400 use opaque liquid silicone to ensure the required structural strength of the mask, while ensuring that the light is focused on the face to prevent the light from damaging others and the user's own eyes. The first mask 100 is also equipped with connection openings 130 on both sides, allowing the user to better fix the first mask on the face through the connection openings 130 when wearing. After the circuit layer 300 is attached to the installation groove, liquid silicone is poured into the first mask and the installation groove for second molding to produce the second mask 200, forming a structure that three-layer integrated liquid silicone wraps the circuit layer. As a whole, the process and structure of relying on buckle or bolt connection in the traditional manufacturing process are omitted, the manufacturing process is simplified, and the internal circuit layer can be protected from be damaged easily. A power installation part 140 is fixedly connected below the nose and mouth hollow opening 120. The circuit layer 300 is equipped with a flexible circuit board 320 electrically connected to the wire 330. The circuit board 320 is equipped with a connection head 340. The lamp bead 310 is an LED light with adjustable light color. The power installation part 140 facilitates the installation of the flexible circuit board 320. The circuit board 320 and the wire 330 are both made of flexible and bendable materials. The lamp bead 310 is electrically connected to flexible circuit board 320 through the flexible wire 330. The connection head 340 is a Type-C interface or a Mini USB interface and is electrically connected to the circuit board 320. The connection head 340 is used for connecting to an external power source.

When the ultra light liquid silicone beauty mask provided in the present invention is in actual use, the power is connected through the connection part 420, and the color, intensity, and time of the light are set. Then a strap for wearing is used to connect with the connection openings 130 on both sides, the eyes are aligned with the eye protection mask 400, the beauty mask is put on the face, a light switch is turned on to start the beauty, and after the set time is over, the light will automatically turn off. Finally, the beauty mask is removed.

In summary, this technical solution adopts the grid format design with the silicone strips 160 vertically cross-connected to each other, making the overall weight of the beauty mask lighter. During production, the second mask 200 is formed by second molding after the circuit layer 300 is attached to the installation groove 150 on the mold, forming the structure that three-layer integrated liquid silicone wraps the circuit layer. The manufacturing process is simple. The detachable eye protection cover 400 is used in conjunction to provide comprehensive protection for the human eye area. At the same time, the first mask 100, the second mask 200, and the eye protection mask 400 are all made of liquid silicone material, which enhances the flexibility of the beauty mask as a whole, and can effectively solve the problems of existing beauty masks in the background art, such as heavy overall weight, complex manufacturing processes, insufficient eye protection, difficult cleaning, and inability to fully fit with the face. The above description only describes embodiments of the present disclosure, and is not intended to limit the present disclosure; various modifications and changes can be made to the present disclosure. Any modifications, equivalent substitutions, and improvements made within the spirit and scope of the present disclosure are intended to be included within the scope of the present disclosure.

What is claimed is:
1. A facial beauty mask, comprising:
a light source part; and
a mask main body; wherein the mask main body is connected to the light source part; the mask main body is provided with a first hollow part and a second hollow part, the first hollow part is used for exposing eyes, and the second hollow part is used for exposing a nose and a mouth; the mask main body is also provided with a breathable hollow part; and the breathable hollow part, the first hollow part and the second hollow part are spaced apart from each other;

wherein the breathable hollow part comprises a plurality of breathable hollow openings, and the plurality of breathable hollow openings are spaced apart from each other;

wherein the plurality of breathable hollow openings at least comprise a first breathable opening unit and a second breathable opening unit, and the first breathable opening unit and the second breathable opening unit are different in shape;

wherein the plurality of breathable hollow openings also comprise a third breathable opening unit; the first breathable opening unit, the second breathable opening unit, and the third breathable opening unit are different from each other in shape; the plurality of breathable hollow openings also comprise a fourth breathable opening unit; and the first breathable opening unit, the second breathable opening unit, the third breathable opening unit, and the fourth breathable opening unit are different from each other in shape;

wherein a plurality of protruding parts extend from the surface of the mask main body, the plurality of protruding parts are spaced apart from each other, a light source installation groove is formed between the plurality of protruding parts, the light source part is positioned inside the light source installation groove, and the light source part is connected to the mask main body; a cover layer is positioned inside the light source installation groove, the light source part is positioned between the cover layer and the mask main body, and the cover layer seals and covers the light source part inside the light source installation groove; the protruding parts comprise a plurality of first protruding units, a plurality of second protruding units, a plurality of third protruding units, and a plurality of fourth protruding units; the first protruding unit extends from an edge of the first breathable opening unit, the second protruding unit extends from an edge of the second breathable opening unit, the third protruding unit extends from an edge of the third breathable opening unit, and the fourth protruding unit extends from an edge of the fourth breathable opening unit; the light source part comprises a plurality of LED light-emitting beads; and the first protruding unit, the second protruding unit, the third protruding unit, and the fourth protruding unit are arranged at intervals around the LED light-emitting bead.

2. The facial beauty mask according to claim 1, wherein the mask main body is provided with a first top wall, a first bottom wall, and a first side wall connected to the first top wall and the first bottom wall; the breathable hollow part comprises a first breathable part, and the first breathable part is positioned between the first hollow part and the first top wall.

3. The facial beauty mask according to claim 1, wherein the breathable hollow part also comprises a second breathable part, and the second breathable part is positioned between the first hollow part and the first side wall.

4. The facial beauty mask according to claim 1, wherein the breathable hollow part also comprises a third breathable part, and the third breathable part is positioned between the first hollow part and the first bottom wall.

5. The facial beauty mask according to claim 1, wherein the breathable hollow openings are defined around the first hollow part and the second hollow part.

6. The facial beauty mask according to claim 1, wherein the breathable hollow part, the first hollow part, and the second hollow part are different from each other in shape.

7. The facial beauty mask according to claim 1, further comprising an eye rest bracket, wherein the eye rest bracket is equipped with an eye rest main body part, a left eye rest part, and a right eye rest part; the left eye rest part and the right eye rest part are both connected to the eye rest main body part, and the eye rest main body part is connected to the mask main body.

8. The facial beauty mask according to claim 7, wherein the eye rest main body part, the left eye rest part, and the right eye rest part are integrally formed.

9. The facial beauty mask according to claim 8, wherein the first hollow part comprises a first left eye hollow opening and a first right eye hollow opening, the left eye rest part is provided with a second left eye hollow opening, the right eye rest part is provided with a second right eye hollow opening, the second left eye hollow opening is aligned with the first left eye hollow opening, and the second right eye hollow opening is aligned with the first right eye hollow opening.

10. The facial beauty mask according to claim 1, further comprising an eye rest bracket, wherein the eye rest bracket is provided with a first front surface and a first rear surface, the first front surface is connected to the mask main body, and a spacing is defined between the first rear surface and the mask main body.

11. The facial beauty mask according to claim 10, wherein the eye rest bracket is a flexible eye rest bracket; and the eye rest bracket is an opaque eye rest bracket.

12. The facial beauty mask according to claim 1, wherein the second hollow part comprises a relatively narrow upper portion and a relatively wide lower portion, so that a relatively narrow nose hollow opening is formed at an upper end of the second hollow part, a relatively wide mouth hollow opening is formed at a lower end of the second hollow part, and the nose hollow opening and the mouth hollow opening are in communication with each other.

13. The facial beauty mask according to claim 1, comprising the cover layer being a light-transmissible cover layer, wherein the cover layer is connected to the mask main body, and the cover layer covers the light source part; the mask main body is provided with a power port and a power input terminal, and the power input terminal is positioned at the power port; the power input terminal is electrically connected to the light source part, and the power input terminal is positioned between the cover layer and the mask main body; the mask main body is integrally formed, and the cover layer is integrally formed; when the cover layer is integrally formed, at least one part of the cover layer is attached to a surface of the mask main body and connected to the mask main body, a position limiting cavity is formed between the cover layer and the mask main body, and the power input terminal is positioned inside the position limiting cavity.

14. The facial beauty mask according to claim 1, further comprising a tightening band, wherein the tightening band is provided with a first end and a second end, the first end is connected to one side of the mask main body, the second end is connected to an opposite side of the mask main body, and a tightening space for wearing is surrounded and formed between the tightening band and the mask main body; one side of the mask main body is provided with a first hanging opening, an opposite side of the mask main body is provided with a second hanging opening, the first end passes through the first hanging opening and is detachably connected to the tightening band, and the second end passes through the second hanging opening and is detachably connected to the tightening band, so that the mask main body and the tightening band are combined into a whole.

15. The facial beauty mask according to claim 14, wherein the tightening band is equipped with a plurality of adjustment connection parts, the plurality of adjustment connection parts are arranged in sequence from the first end to the second end, the first end passes through the first hanging opening and is connected to one of the plurality of adjustment connection parts, and the second end passes through the second hanging opening and is connected to one of the plurality of adjustment connection parts, so that a size of the tightening space is adjusted; an inner surface of the tightening band is provided with a hook and loop fastener, the plurality of adjustment connection parts are a plurality of hook bands of the hook and loop fastener, the first end is equipped with a first hook engaging band, the second end is equipped with a second hook engaging band, the first hook engaging band passes through the first hanging opening and is connected to one of the plurality of hook bands, and the second hook engaging band passes through the second hanging opening and is connected to one of the plurality of hook bands.

16. The facial beauty mask according to claim 14, wherein the tightening band is provided with a middle part, a left part, and a right part; the left part is connected to one side of the middle part, the right part is connected to an opposite side of the middle part, the first end is provided on the left part, and the second end is provided on the right part; and the middle part, the left part, and the right part are integrally formed.

* * * * *